(12) United States Patent
McDonald (10) Patent No.: US 9,190,793 B2
(45) Date of Patent: Nov. 17, 2015

(54) SYSTEMS AND METHODS FOR COUPLING COILED CONDUCTORS TO CONDUCTIVE CONTACTS OF AN ELECTRICAL STIMULATION SYSTEM

(71) Applicant: BOSTON SCIENTIFIC NEUROMODULATION CORPORATION, Valencia, CA (US)

(72) Inventor: Matthew Lee McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 280 days.

(21) Appl. No.: 13/769,030

(22) Filed: Feb. 15, 2013

(65) Prior Publication Data
US 2013/0152387 A1 Jun. 20, 2013

Related U.S. Application Data

(62) Division of application No. 12/536,290, filed on Aug. 5, 2009, now Pat. No. 8,380,325.

(51) Int. Cl.
*H01R 43/20* (2006.01)
*A61N 1/05* (2006.01)
*H01R 43/00* (2006.01)

(52) U.S. Cl.
CPC *H01R 43/00* (2013.01); *A61N 1/05* (2013.01); *Y10T 29/49117* (2015.01); *Y10T 29/49208* (2015.01)

(58) Field of Classification Search
CPC ......... H01R 43/20; H01R 43/005; A61N 1/05
USPC ................... 29/876, 877, 878, 879, 883, 884; 607/119
See application file for complete search history.

(56) References Cited

U.S. PATENT DOCUMENTS

| | | |
|---|---|---|
| 4,033,355 A | 7/1977 | Amundson |
| 4,106,512 A | 8/1978 | Bisping |

(Continued)

FOREIGN PATENT DOCUMENTS

| | | |
|---|---|---|
| EP | 37223 A1 | 10/1981 |
| EP | 178528 A1 | 4/1986 |

(Continued)

OTHER PUBLICATIONS

U.S. Appl. No. 12/536,290, Official Communication mailed Mar. 15, 2012.

(Continued)

*Primary Examiner* — Peter DungBa Vo
*Assistant Examiner* — Kaying Kue
(74) *Attorney, Agent, or Firm* — Lowe Graham Jones PLLC; Bruce E. Black (57) ABSTRACT

An implantable lead includes an elongated member. A plurality of electrodes are disposed on a distal end of the elongated member. A plurality of terminals are disposed on a proximal end of the elongated member. Each of a plurality of conductors electrically couples at least one of the electrodes to at least one of the terminals. The plurality of conductors are disposed in the elongated member in a coiled configuration and have an end portion. Each of a plurality of constraining elements is disposed over at least one of the plurality of conductors such that the underlying at least one of the plurality of conductors is maintained in the coiled configuration. At least one of the plurality of electrodes or terminals is disposed over the constraining element and electrically coupled to at least one of the plurality of conductors.

17 Claims, 9 Drawing Sheets

(56) References Cited

U.S. PATENT DOCUMENTS

| | | | |
|---|---|---|---|
| 4,146,036 A | 3/1979 | Dutcher et al. | |
| 4,402,329 A | 9/1983 | Williams | |
| 4,437,474 A * | 3/1984 | Peers-Trevarton | A61N 1/056 29/605 |
| 4,458,695 A | 7/1984 | Peers-Trevarton | |
| 4,479,500 A | 10/1984 | Smits | |
| 4,484,586 A * | 11/1984 | McMickle | A61L 29/085 156/51 |
| 4,566,467 A | 1/1986 | DeHaan | |
| 4,614,395 A | 9/1986 | Peers-Trevarton | |
| 4,630,611 A * | 12/1986 | King | A61B 5/076 600/377 |
| 4,938,822 A | 7/1990 | Peers-Trevarton | |
| 4,945,342 A * | 7/1990 | Steinemann | H01B 7/0009 174/113 AS |
| 5,000,177 A | 3/1991 | Hoffmann et al. | |
| 5,016,646 A | 5/1991 | Gotthardt et al. | |
| 5,020,544 A | 6/1991 | Dahl et al. | |
| 5,020,545 A | 6/1991 | Soukup | |
| 5,282,845 A | 2/1994 | Bush et al. | |
| 5,324,321 A | 6/1994 | Pohndorf et al. | |
| 5,330,522 A | 7/1994 | Kreyenhagen | |
| 5,366,496 A | 11/1994 | Dahl et al. | |
| 5,387,234 A | 2/1995 | Hirschberg | |
| 5,405,372 A | 4/1995 | Gilljam et al. | |
| 5,456,708 A | 10/1995 | Doan et al. | |
| 5,496,362 A | 3/1996 | KenKnight et al. | |
| 5,716,390 A | 2/1998 | Li | |
| 5,987,746 A * | 11/1999 | Williams | A61N 1/0568 29/825 |
| 6,083,247 A | 7/2000 | Rutten et al. | |
| 6,181,969 B1 | 1/2001 | Gord | |
| 6,253,111 B1 | 6/2001 | Carner | |
| 6,357,447 B1 * | 3/2002 | Swanson | A61B 5/0422 128/898 |
| 6,456,888 B1 | 9/2002 | Skinner et al. | |
| 6,477,427 B1 * | 11/2002 | Stolz | A61N 1/05 607/116 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,687,550 B1 | 2/2004 | Doan | |
| 6,741,892 B1 | 5/2004 | Meadows et al. | |
| 6,909,920 B2 | 6/2005 | Lokhoff et al. | |
| 6,920,361 B2 * | 7/2005 | Williams | A61N 1/05 600/373 |
| 7,155,293 B2 | 12/2006 | Westlund et al. | |
| 7,184,838 B2 | 2/2007 | Cross, Jr. | |
| 7,225,035 B2 | 5/2007 | Brabec et al. | |
| 7,244,150 B1 | 7/2007 | Brase et al. | |
| 7,289,846 B2 | 10/2007 | Shoberg et al. | |
| 7,512,447 B2 | 3/2009 | Marshall et al. | |
| 7,546,165 B2 * | 6/2009 | Zarembo | A61N 1/056 607/122 |
| 7,761,165 B1 | 7/2010 | He et al. | |
| 7,831,311 B2 * | 11/2010 | Cross, Jr. | A61N 1/056 607/116 |
| 7,974,704 B2 | 7/2011 | Alexander et al. | |
| 8,316,537 B2 * | 11/2012 | Black | A61N 1/05 29/858 |
| 8,478,425 B2 * | 7/2013 | Klardie | A61N 1/0551 607/115 |
| 8,910,376 B2 * | 12/2014 | McDonald | H01R 24/58 29/842 |
| 8,918,187 B2 * | 12/2014 | Klardie | A61N 1/05 607/116 |
| 8,968,331 B1 * | 3/2015 | Sochor | A61N 1/0534 606/129 |
| 2002/0099430 A1 | 7/2002 | Verness | |
| 2002/0151949 A1 | 10/2002 | Dahl et al. | |
| 2003/0114905 A1 | 6/2003 | Kuzma | |
| 2003/0144719 A1 | 7/2003 | Zeijlemaker | |
| 2004/0059392 A1 | 3/2004 | Parramon et al. | |
| 2004/0249430 A1 | 12/2004 | Martinez et al. | |
| 2004/0260374 A1 | 12/2004 | Zhang et al. | |
| 2005/0113896 A1 | 5/2005 | Pavlik et al. | |
| 2005/0165465 A1 | 7/2005 | Pianca et al. | |
| 2006/0089691 A1 | 4/2006 | Kaplan et al. | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0219595 A1 | 9/2007 | He | |
| 2007/0239243 A1 | 10/2007 | Moffitt et al. | |
| 2007/0255369 A1 | 11/2007 | Bonde et al. | |
| 2008/0033497 A1 | 2/2008 | Bulkes et al. | |
| 2008/0071320 A1 | 3/2008 | Brase | |
| 2008/0178449 A1 | 7/2008 | Huotari et al. | |
| 2009/0012591 A1 | 1/2009 | Barker | |
| 2009/0082655 A1 | 3/2009 | Seifert et al. | |
| 2009/0157156 A1 | 6/2009 | Foster | |
| 2011/0034978 A1 | 2/2011 | McDonald | |

FOREIGN PATENT DOCUMENTS

| | | |
|---|---|---|
| EP | 570712 A1 | 11/1993 |
| EP | 1187655 A1 | 3/2002 |
| WO | 9906104 A1 | 2/1999 |

OTHER PUBLICATIONS

U.S. Appl. No. 12/536,290, Official Communication mailed Aug. 16, 2012.

International Application No. PCT/US2010/043875, International Search Report and Written Opinion mailed Nov. 22, 2011.

* cited by examiner

SYSTEMS AND METHODS FOR COUPLING COILED CONDUCTORS TO CONDUCTIVE CONTACTS OF AN ELECTRICAL STIMULATION SYSTEM

CROSS-REFERENCE TO RELATED APPLICATIONS

This patent application is a divisional of U.S. patent application Ser. No. 12/536,290 filed on Aug. 5, 2009, which is incorporated herein by reference.

FIELD

The present invention is directed to the area of implantable electrical stimulation systems and methods of making and using the systems. The present invention is also directed to implantable electrical stimulations with leads having coiled conductors coupled to conductive contacts disposed on the leads, as well as methods of making and using the conductors, conductive contacts, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes an elongated member having a distal end, a proximal end, and a longitudinal length. A plurality of electrodes are disposed on the distal end of the elongated member. A plurality of terminals are disposed on the proximal end of the elongated member. Each of a plurality of conductors electrically couples at least one of the electrodes to at least one of the terminals. The plurality of conductors are disposed in the elongated member in a coiled configuration and have an end portion. A plurality of constraining elements are disposed along at least one of the distal end or the proximal end of the elongated member. Each of the constraining elements is disposed over at least one of the plurality of conductors such that the underlying at least one of the plurality of conductors is maintained in the coiled configuration beneath the constraining element. At least one of the plurality of electrodes or at least one of the plurality of terminals is disposed over the constraining element and electrically coupled to at least one of the plurality of conductors.

In another embodiment, an electrical stimulating system includes an elongated member having a distal end, a proximal end, and a longitudinal length. A plurality of electrodes are disposed on the distal end of the elongated member. A plurality of terminals are disposed on the proximal end of the elongated member. Each of a plurality of conductors electrically couples at least one of the electrodes to at least one of the terminals. The plurality of conductors are disposed in the elongated member in a coiled configuration and have an end portion. A plurality of constraining elements are disposed along at least one of the distal end or the proximal end of the elongated member. Each of the constraining elements is disposed over at least one of the plurality of conductors such that the underlying at least one of the plurality of conductors is maintained in the coiled configuration beneath the constraining element. At least one of the plurality of electrodes or at least one of the plurality of terminals is disposed over the constraining element and electrically coupled to at least one of the plurality of conductors. A control module is configured and arranged to electrically couple to the proximal end of the elongated member. The control module includes a housing and an electronic subassembly disposed in the housing. A connector is configured and arranged to receive the elongated member. The connector has a proximal end, a distal end, and a longitudinal length. The connector includes a connector housing and a plurality of connector contacts disposed in the connector housing. The connector housing defines a port at the distal end of the connector. The port is configured and arranged for receiving the proximal end of the elongated member. The connector contacts are configured and arranged to couple to at least one of the plurality of terminals disposed on the proximal end of the elongated member.

In yet another embodiment, a method for forming an implantable lead includes placing a plurality of elongated conductors into a coiled configuration. A first constraining element is disposed over the plurality of conductors in proximity to an end portion of the conductors. A first conductor of the plurality of conductors is uncoiled to the first constraining element from a location closer to the end portion than the first constraining element. A second constraining element is disposed over a portion of the plurality of conductors such that the second constraining element is axially spaced apart from the first constraining element and is disposed closer to the end portion of the conductors than the first constraining element. The uncoiled end of the first conductor extends radially from the elongated coiled conductors between the first constraining element and the second constraining element. A second conductor of the plurality of conductors is uncoiled to the second constraining element from a location closer to the end portion than the second constraining element. A first conductive contact is disposed over the first constraining element. The uncoiled portion of the first conductor is electrically coupled to the first conductive contact.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulations with leads having coiled conductors coupled to conductive contacts disposed on the leads, as well as methods of making and using the conductors, conductive contacts, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710; and U.S. Patent Application Publications Nos. 2005/0165465 and 2007/0150036, all of which are incorporated by reference.

Figure 1:
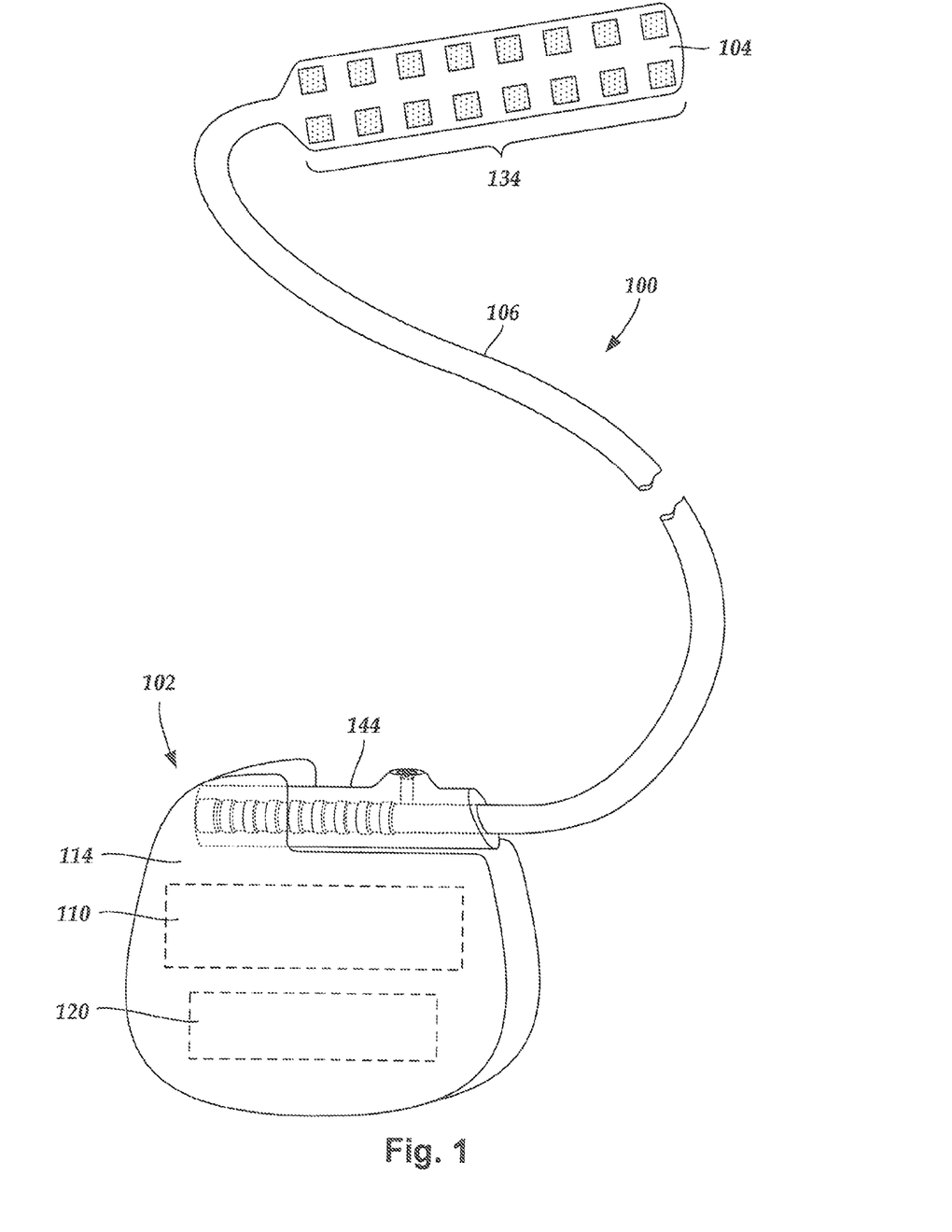
FIG. 1 is a schematic view of one embodiment of an electrical stimulation system, according to the invention.
Figure 2:
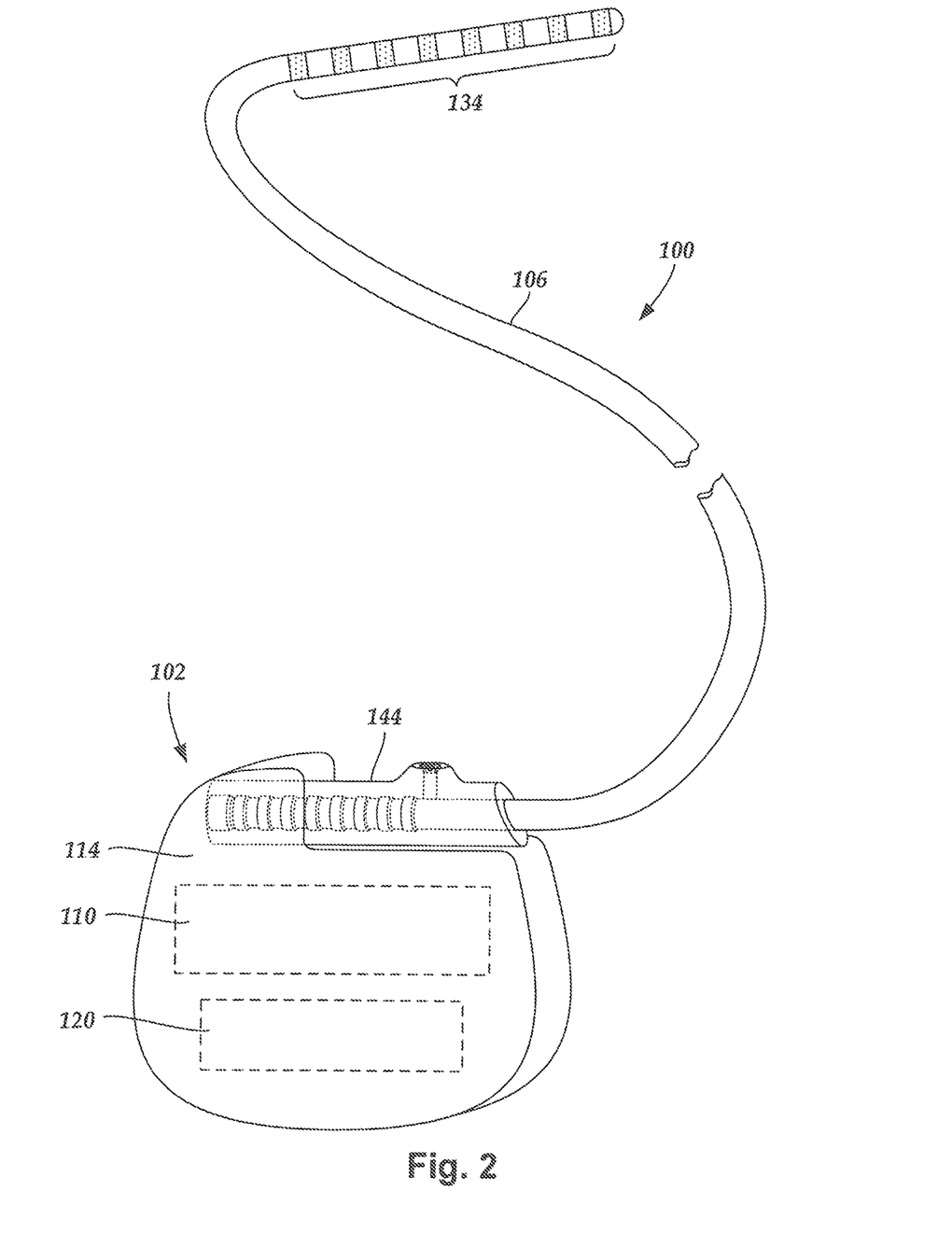
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIGS. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A and 336 of FIG. 3B) are typically disposed at the proximal end of the one or more lead bodies 106 for connection to corresponding conductive contacts (e.g., 314 in FIGS. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIGS. 3A and 336 of FIG. 3B) to the electrodes 134. Typically, one or more electrodes 134 are electrically coupled to a terminal (e.g., 310 in FIGS. 3A and 336 of FIG. 3B). In some embodiments, each terminal (e.g., 310 in FIGS. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
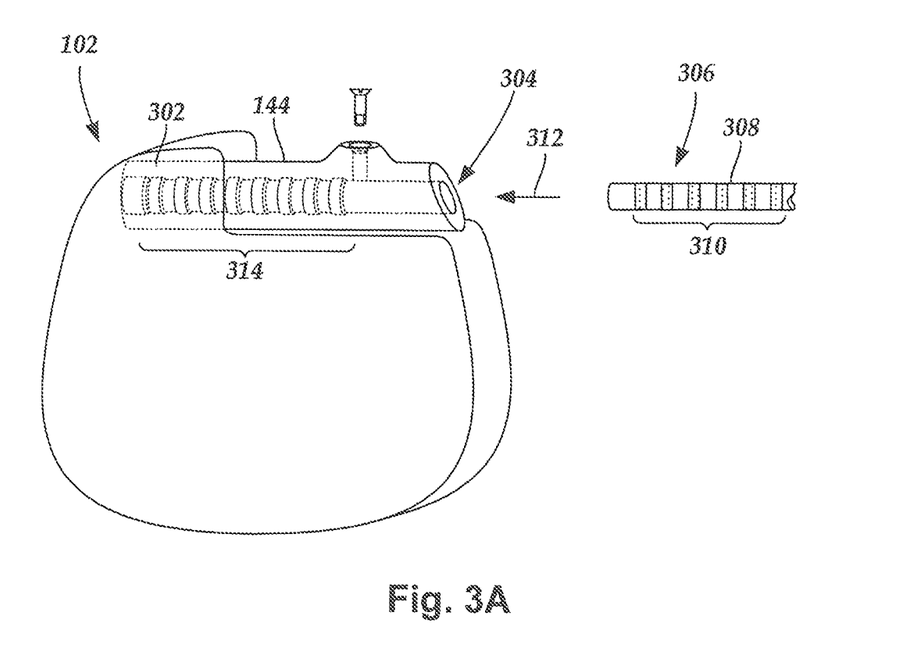
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. Nos. 7,244,150 and 8,224,450, which are incorporated by reference.

Figure 3B:
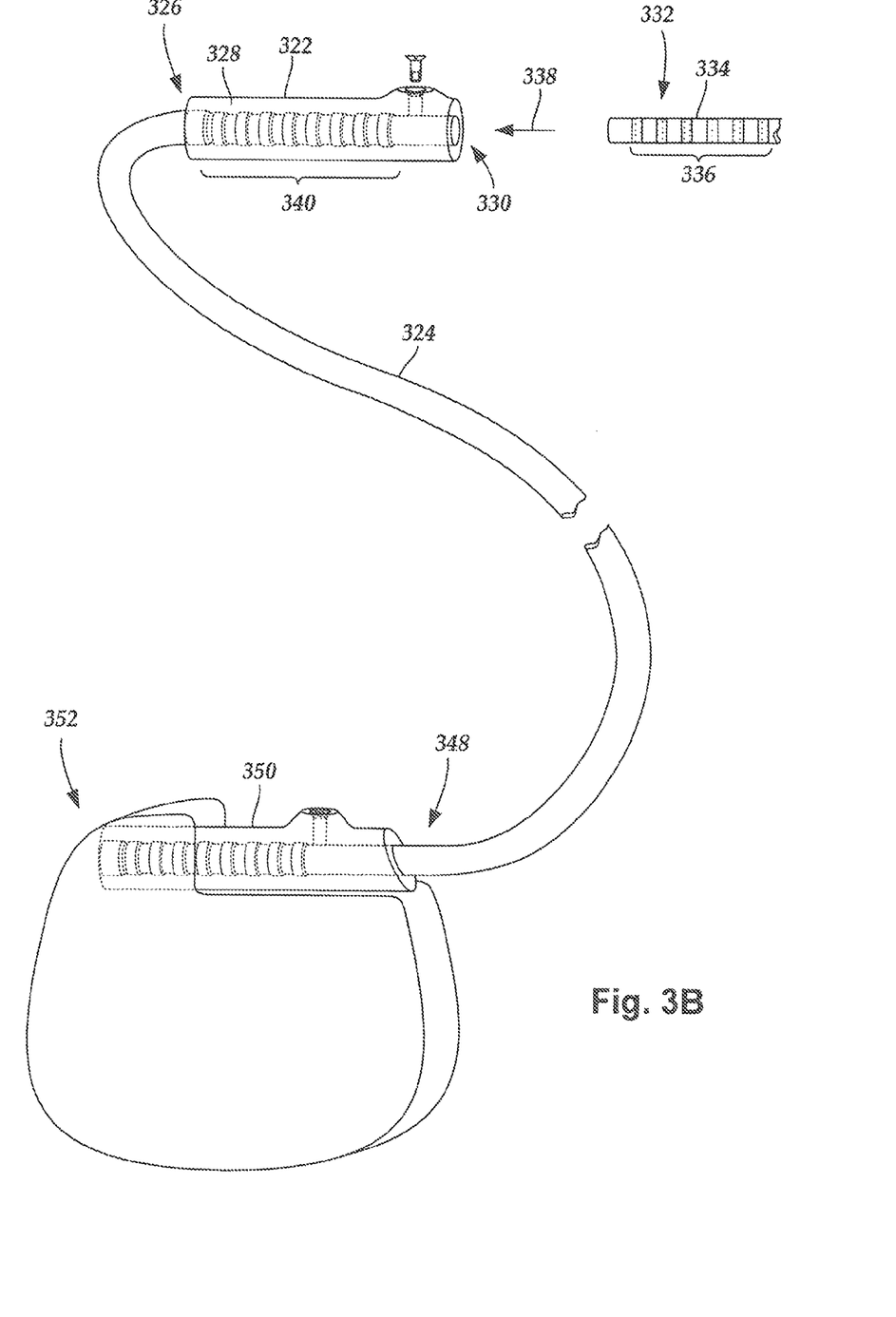
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include one or more single-layer regions flanking at least one end of the multi-layer region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
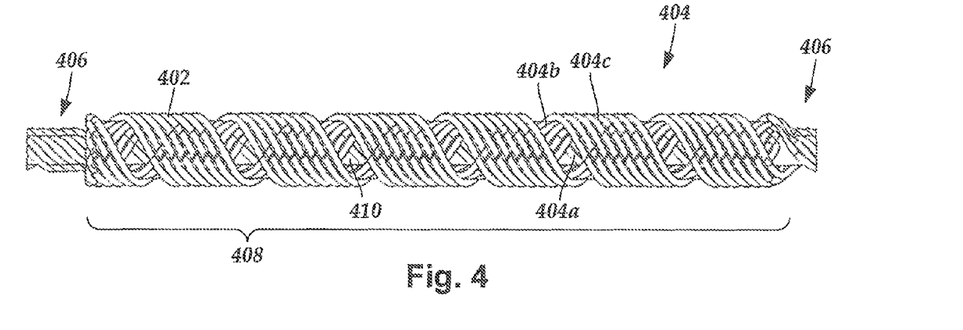
FIG. 4 is a schematic side view of one embodiment of portions of a plurality of conductors configured into a multi-layer region of overlapping conductor segments, according to the invention.

FIG. 4 schematically illustrates one embodiment of a plurality of conductors 402. The conductors 402 are configured into a plurality of units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 406, separated from one another by a multi-layer region, such as the multi-layer region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member are configured into units. In at least some embodiments, only a subset of the conductors disposed in an elongated member include one or more units, the remaining conductors having a different arrangement (for example, a single conductor segment between the terminal(s) and electrode(s)/conductive contact(s)).

In at least some embodiments, one or more arrays of conductive contacts (e.g., terminals, electrodes, or the like) are coupled to conductors that are coiled along at least a portion of a lead. In at least some embodiments, the conductive contact arrays are formed over single-layer regions of coiled conductors. In at least some embodiments, each of the conductors is coiled until the conductor is in proximity to the conductive contact to which that conductor is coupled. Thus, in at least some embodiments, the conductors are coupled to the conductive contacts such that the conductors do not include substantially-straight sections extending along a longitudinal axis of the lead (or lead extension).

As discussed above, providing conductors in a lead (or lead extension) that are configured into units may reduce unwanted heating, induced currents, or premature failure of electronic components caused by transient signals generated from RF pulses encountered, for example, during an MRI procedure. Accordingly, it may be an advantage to reduce, or even eliminate, portions of the conductor that are not configured into units. Additionally, forming units with coiled conductors may have the added benefit of reducing physical stresses that occur along portions of the conductors when a lead (or lead extension) is deformed (e.g., bent, squeezed, or the like) as compared to leads (or lead extensions) having substantially-straight conductors.

Figure 5:
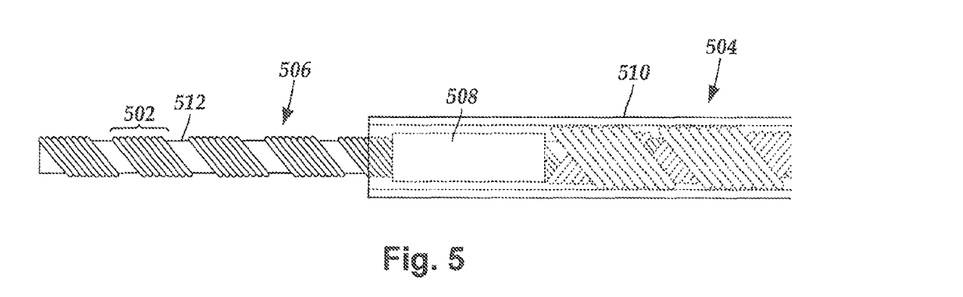
FIG. 5 is a schematic side view of one embodiment of portions of a plurality of coiled conductors, the coiled conductors including a retaining element disposed over a portion of a single-layer region and preventing a neighboring multi-layer region from unraveling, according to the invention.

In at least some embodiments, the coiled conductors are configured into units. In preferred embodiments, when the coiled conductors are configured into units, conductive contact arrays are disposed over single-layer regions of the units. FIG. 5 is a schematic side view of one embodiment of a portion of a plurality of coiled conductors 502. The coiled conductors 502 include a multi-layer region 504 and a single-layer region 506. In at least some embodiments, a retaining element 508 is disposed over a portion of the single-layer region 506 in proximity to the boundary between the multi-layer region 504 and the single-layer region 506 to prevent the multi-layer region 504 from unraveling.

In at least some embodiments, a jacket 510 is disposed over the multi-layer region 504 to protect the multi-layer region 504. In at least some embodiments, the jacket 510 helps to prevent the multi-layer region 504 from unraveling. The jacket 504 can be formed from any flexible biocompatible material suitable for disposing over conductors, such as polyurethane. In at least some embodiments, when the jacket 510 and the retaining element 508 are both disposed over a portion of the conductors 502, the jacket 510 is disposed over at least a portion of the retaining element 508. In at least some embodiments, the conductors 502 are coiled around a conductor placement sleeve 512. In at least some embodiments, the conductor placement sleeve 512 defines a lumen configured and arranged to receive a stiffening member (e.g., a stylet, or the like).

Figure 6:
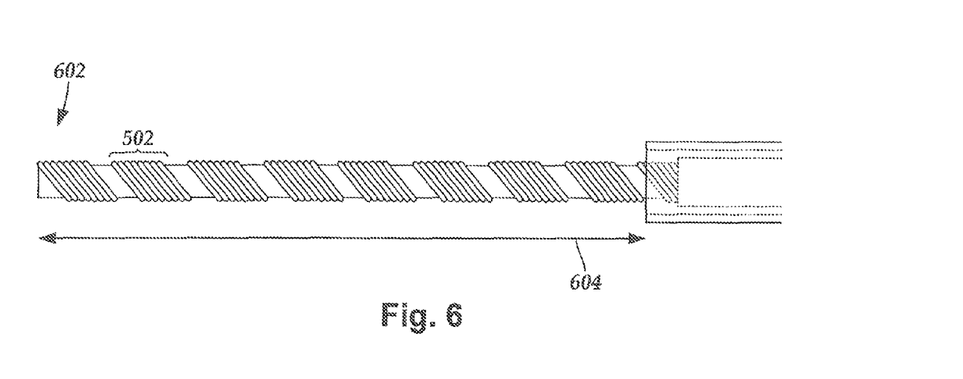
FIG. 6 is a schematic side view of one embodiments of an end portion of the coiled conductors of FIG. 5, the end portion including a single-layer region suitable for fabricating an array of conductive contacts over, according to the invention.

FIG. 6 is a schematic side view of one embodiment of an end portion 602 of the conductors 502. In at least some embodiments, the single-layer region 506 extends to the end portion 602 of the conductors 502. In at least some embodiments, the single-layer region 506 has a longitudinal length 604 suitable for fabricating an array of conductive contacts (1008 in FIG. 10). It will be understood that the end portion 602 can be either a proximal end or a distal end of a lead (a paddle lead or a percutaneous lead) or a lead extension.

In at least some embodiments, the conductive contact array is fabricated over the single-layer region 506 by uncoiling the conductors 502 from (or in proximity to) the end portion 602 and separating the uncoiled portions of the conductors 502 from one another by disposing spaced-apart constraining elements (see e.g., 702 and 802-804 of FIG. 8) along the single-layer region 506 such that the uncoiled portion of a different one of the conductors 502 is disposed between each pair of spaced-apart constraining elements. The conductive contact array is then disposed over the constraining elements and electrically coupled to the uncoiled portions of the conductors 502.

The constraining elements can be formed from any material suitable for disposing over a plurality of coiled conductors tightly enough to prevent an uncoiled end of a conductor from uncoiling beyond the constraining element. Examples of possible materials that can be used to form constraining elements include, for example, silicone tubing, thermoplastic polymers, shrink tubing, one or more adhesives, plastic, metals, alloys, composites, and the like or combinations thereof. In at least some embodiments, each of the constraining elements is formed from the same material(s). In at least some embodiments, at least one of the constraining elements is formed from one or more different materials than another one of the constraining elements. In at least some embodiments, the retaining element (508 in FIG. 5) is formed from the same material as at least one of the constraining elements.

The constraining elements can be disposed over the conductors 502 in any manner. For example, the constraining elements can be disposed over the conductors 502 by heat shrinking, reflowing, injection, injection molding, crimping, swaging, twisting, rolling, sliding, tying, and the like or combinations thereof. In at least some embodiments, the retaining element (508 in FIG. 5) is formed in the same manner as at least one of the constraining elements. In at least some embodiments, at least one of the retaining element or the constraining elements can be C-shaped. In at least some embodiments, at least one of the retaining element or the constraining elements can define one or more slits.

Figure 7:
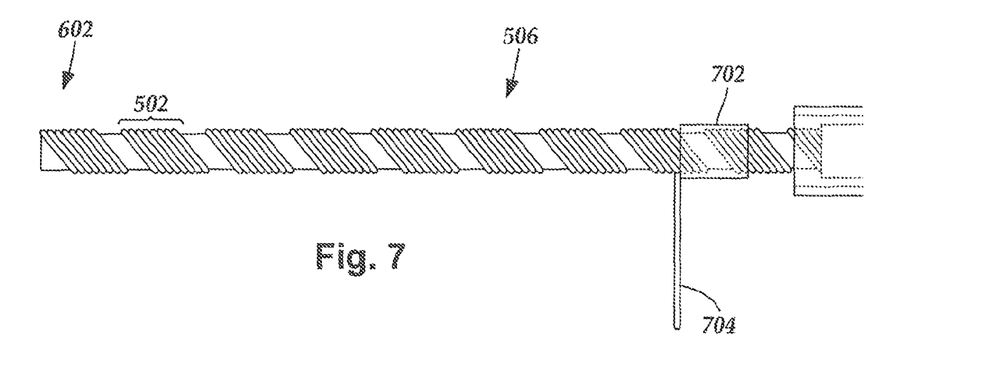
FIG. 7 is a schematic side view of one embodiment of a constraining element disposed over the portions of the coiled conductors of FIG. 6 in proximity to the end portion of the conductors, one of the conductors being uncoiled to the constraining element from a location closer to the end portion and radially extended from the coiled conductors, according to the invention.

In at least some embodiments, a constraining element is disposed over a portion of the single-layer region 506 and one of the conductors 502 is uncoiled to the constraining element. FIG. 7 is a schematic side view of one embodiment of a first constraining element 702 disposed over the single-layer region 506 of the conductors 502 in proximity to the end portions of the conductors. A conductor 704 of the plurality of conductors 502 is uncoiled to the first constraining element 702 from a location closer to the end portion 602. In at least some embodiments, the conductor 704 is cut at a location closer to the end portion 602 and then uncoiled. In at least some embodiments, the conductor 704 is extended radially from a longitudinal axis of the plurality of conductors 502.

Once the constraining element 702 is disposed over the plurality of conductors 502 and one of the conductors 704 of the plurality of conductors 512 is uncoiled to the first constraining element 702, a second constraining element can be disposed over the plurality of conductors 502 axially from the first constraining element 702 and positioned closer to the end portion 602 than the first constraining element 702 such that the uncoiled portion of the conductor 704 is positioned between the first constraining element 702 and the second constraining element. A second conductor of the plurality of conductors 502 can be uncoiled to the second constraining element from a location closer to the end portion 602. A third constraining element can be positioned axially to the second constraining element such that the uncoiled portion of the second uncoiled conductor is positioned between the second constraining element and the third constraining element.

The above-described steps can be repeated until a desired number of conductors are uncoiled and separated from one another. In at least some embodiments, the steps are repeated until each of the conductors 502 has been uncoiled and separated from one another. In at least some embodiments, the steps are repeated until the number of conductors 502 uncoiled and separated from one another is equal to the number of conductive contacts to be disposed on a lead (or lead extension).

Figure 8:
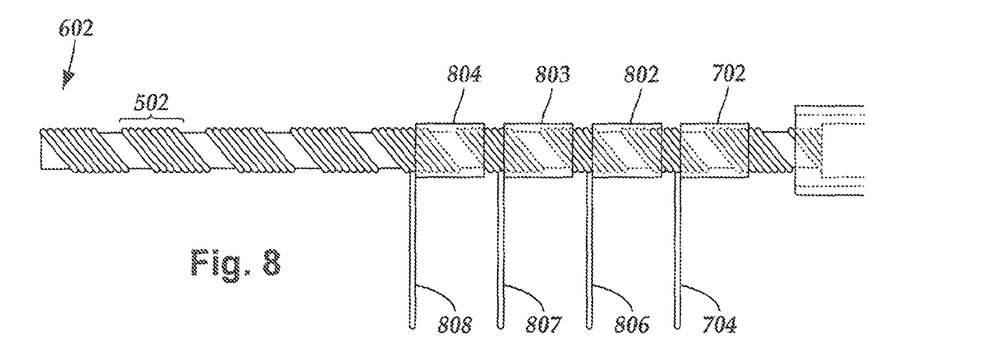
FIG. 8 is a schematic side view of one embodiment of a plurality of constraining elements axially disposed over the portions of the conductors of FIG. 6 in proximity to the end portions of the conductors, each of the constraining elements having a different one of the conductors uncoiled to that constraining element from a location closer to the end portion and radially extended from the coiled conductors such that each uncoiled conductor is separated from another uncoiled conductor by a constraining element, according to the invention.

FIG. 8 is a schematic side view of one embodiment of a plurality of constraining elements 702 and 802-804 axially disposed over the portions of the conductors 502 in proximity to the end portion 602 of the conductors 502. Each of the constraining elements 702 and 802-804 has a different conductor 704 and 806-808, respectively, uncoiled to the constraining elements 702 and 802-804 from locations closer to the end portion 806 than the constraining elements 702 and 802-804 such that the uncoiled portions of each uncoiled conductor 704 and 806-808 are separated from one another by one of the constraining elements 702 and 802-804.

Figure 9:
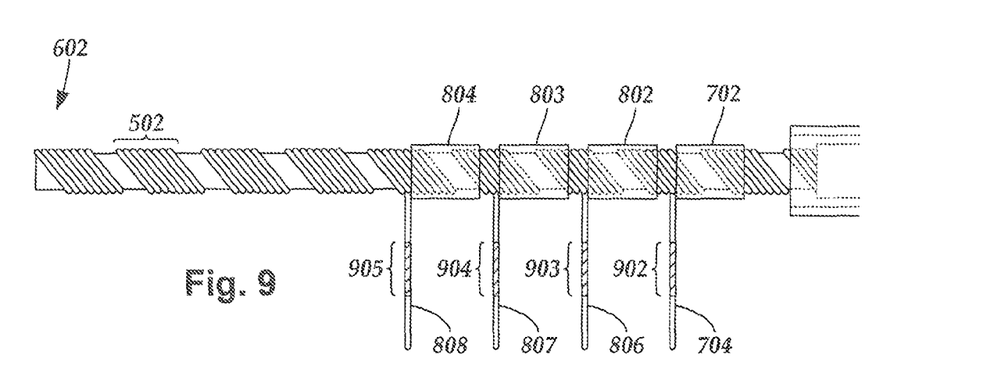
FIG. 9 is a schematic side view of one embodiment of portions of insulation removed from the radially-extended conductors of FIG. 8, according to the invention.

Insulation is typically disposed individually over each of the plurality of coiled conductors 502. In at least some embodiments, a portion of the insulation is removed from the uncoiled portions of the conductors 704 and 806-808 to expose conductive material for coupling to conductive contacts. FIG. 9 is a schematic side view of one embodiment of the plurality of conductors 704 and 806-808 each uncoiled to the constraining elements 702 and 802-804, respectively, from locations closer to the end portion 602 of the plurality of uncoiled conductors 502. Portions of insulation disposed over the conductors 704 and 806-808 are removed from the uncoiled portions of the conductors 704 and 806-808 to form regions 902-905 of exposed conductive material.

Insulation can be removed from the uncoiled portions of the conductors 704 and 806-808 in any manner. For example, insulation can be removed from the uncoiled portions of the conductors 704 and 806-808 by laser ablation, abrasion (e.g., grit blasting, or the like), thermal stripping, chemical stripping, mechanical stripping, and the like or combinations thereof.

Conductive contacts (e.g., terminals, electrodes, or the like) can be disposed over the constraining elements 702 and 802-804. In at least some embodiments, one or more of the conductive contacts are disposed over the constraining elements 702 and 802-804 such that the conductive contacts are aligned over the constraining elements 702 and 802-804. In at least some embodiments, one or more of the conductive contacts are disposed over the constraining elements 702 and 802-804 such that one or more of the conductive contacts are either closer to, or farther away from the end portion 602 of the coiled conductors 502 from the constraining elements 702 and 802-804. In at least some embodiments, one or more of the conductive contacts are not disposed over one or more of the constraining elements 702 and 802-804. In at least some embodiments, the spacing between bordering conductive contacts is the same as the spacing between adjacent constraining elements 702 and 802-804. In at least some embodiments, the spacing between bordering conductive contacts is different from the spacing between bordering constraining elements 702 and 802-804.

The conductive contacts can be of any size and shape. For example, the conductive contacts can be annular, C-shaped, rectangular, circular, ovoid, or any other geometric or irregular shape. In at least some embodiments, the conductive contacts are sized and shaped for use in a percutaneous lead. In at least some embodiments, the conductive contacts are sized and shaped for use in a paddle lead. In at least some embodiments, the conductive contacts are sized and shaped for use in a lead extension.

Figure 10:
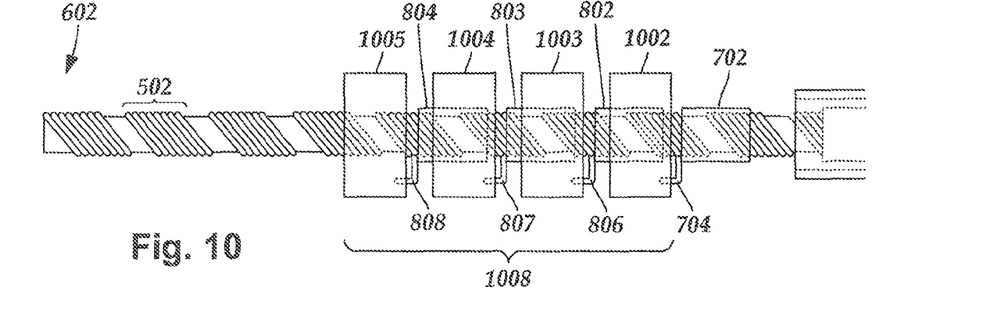
FIG. 10 is a schematic side view of one embodiment of a plurality of conductive contacts disposed over the constraining elements of FIG. 8 to form a conductive contact array, each of the radially-extended conductors of FIG. 9 coupled to a different conductive contact of the conductor contact array, according to the invention.

FIG. 10 is a schematic side view of one embodiment of conductive contacts 1002-1005 partially disposed over, and partially disposed in proximity to, at least some of the constraining elements 702 and 802-804 to form a conductive contact array 1008. The uncoiled portions of the conductors 704 and 806-808 are electrically coupled to the conductive contacts 1002-1005, respectively. Typically, the uncoiled portions of the conductors 704 and 806-808 are electrically coupled to the conductive contacts 1002-1005, respectively, via the exposed portions of the uncoiled conductors 704 and 806-808. The conductors 704 and 806-808 can be electrically coupled to the conductive contacts 1002-1005, respectively, in many different ways including, for example, laser welding, resistance welding, swaging, or the like or combinations thereof.

Figure 11:
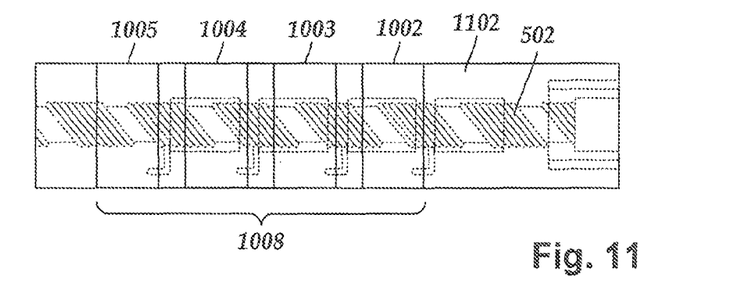
FIG. 11 is a schematic side view of one embodiment of the conductive contact array of FIG. 10 disposed in proximity to the end portion of the conductors of FIG. 6, the conductors encased in a non-conductive material, according to the invention.

In at least some embodiments, a non-conductive material is disposed over the coiled conductors 502 and also between conductive contacts 1002-1005 to electronically isolate the conductive contacts 1002-1005 from one another and to protect the coiled conductors 502. In at least some embodiments, the non-conductive material is disposed over the coiled conductors 502 such that the non-end portions of the coiled conductors 502 have a uniform transverse diameter. In at least some embodiments, the non-conductive material is disposed over the coiled conductors 502 to form an isodiametric lead (or lead extension). FIG. 11 is a schematic side view of one embodiment of non-conductive material 1102 applied over the conductors 502 and between conductive contacts 1002-1005 of the conductive contact array 1008.

The non-conductive material 1102 can be formed from any suitable biocompatible material including, for example, one or more thermoplastics, one or more silicones, one or more plastics, and the like or combinations thereof. Many different methods of application can be used to apply the non-conductive material 1102 including, for example, injection molding, reflowing, dip molding, and the like or combinations thereof. In at least some embodiments, the non-conductive material 1102 can be applied along the entire length of the coiled conductors 502. In at least some embodiments, the non-conductive material 1102 is ground down to be flush with outer surfaces of the conductive contacts. In at least some embodiments, the end portion 602 of the conductors 502 is removed.

Figure 12:
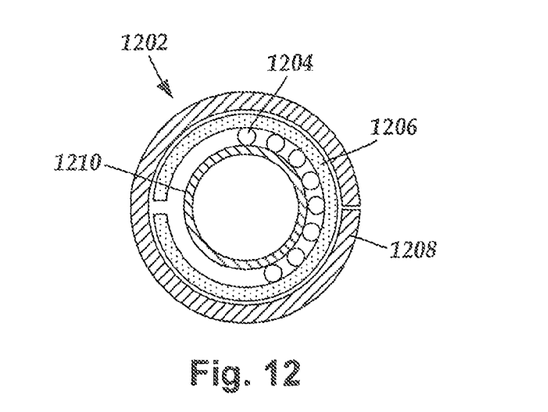
FIG. 12 is a schematic transverse cross-sectional view of another embodiment of a constraining element disposed over a single-layer section of a plurality of coiled conductors, according to the invention.

In at least some embodiments, a portion of the constraining element may be conductive. In at least some embodiments, a constraining element includes a spacer and a conductive member disposed over the spacer. FIG. 12 is a schematic transverse cross-sectional view of another embodiment of a constraining element 1202 disposed over a single-layer section of a plurality of coiled conductors, such as conductor 1204. The constraining element 1202 includes a spacer 1206 and an outer conductive member 1208. In at least some embodiments, the conductors 1204 are disposed over a conductor placement sleeve 1210. In at least some embodiments, the spacer 1206 provides a protective layer between the conductors 1204 and the outer conductive member 1208. In at least some embodiments, the spacer 1206 is a slit spacer. In at least some embodiments, the outer conductive member 1208 is formed from a rigid material, such as one or more metals or alloys. In at least some embodiments, the outer conductive member 1208 is annular. In at least some embodiments, the outer conductive member 1208 is C-shaped. In at least some embodiments, the outer conductive member 1208 is crimped around the spacer 1206.

Figure 13:
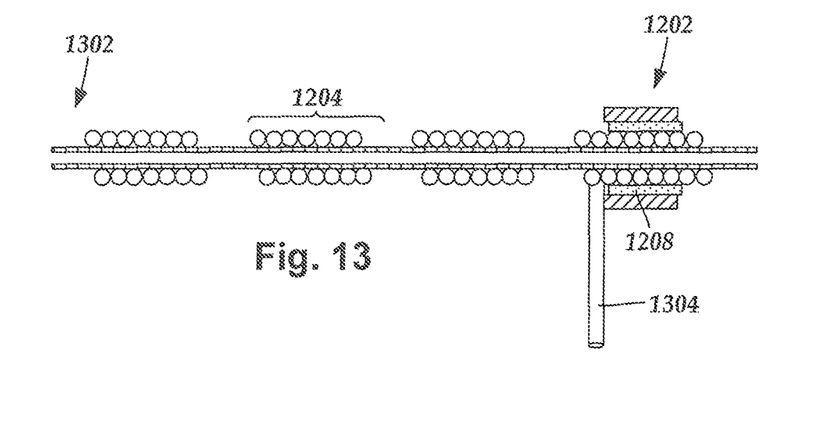
FIG. 13 is a schematic longitudinal cross-sectional view of one embodiment of the constraining element of FIG. 12 disposed over portions of the plurality of coiled conductors of FIG. 12 in proximity to an end portion of the conductors, one of the conductors being uncoiled to the constraining element from a location closer to the end portion and extended radially from the coiled conductors, according to the invention.

FIG. 13 is a schematic longitudinal cross-sectional view of one embodiment of the constraining element 1202 disposed over portions of a plurality of coiled conductors 1204 in proximity to an end portion 1302 of the coiled conductors 1204. One conductor 1304 of the plurality of conductors 1204 is uncoiled to the constraining element 1202 from a location closer to the end portion 1302. In at least some embodiments, the uncoiled portion of the conductor 1304 is electrically coupled to the outer conductive member 1208. The uncoiled portion of the conductor 1304 can be electrically coupled to the outer conductive member 1208 in many different ways including, for example, welding, soldering, brazing, crimping, swaging, or the like or combinations thereof.

Figure 14:
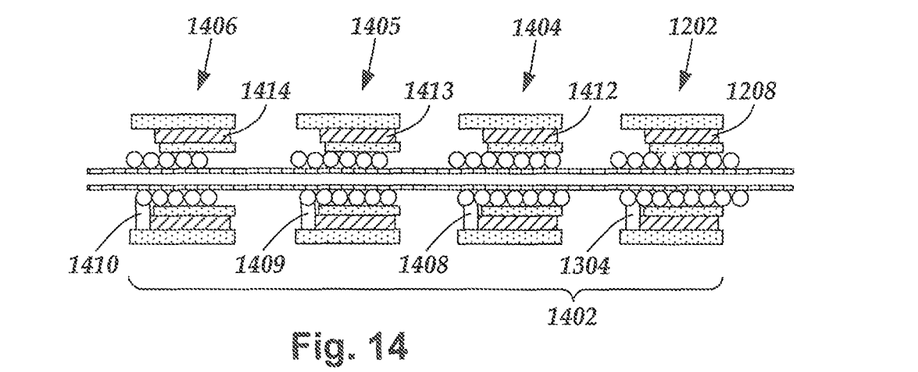
FIG. 14 is a schematic longitudinal cross-sectional view of one embodiment of an array of conductive contacts disposed over spaced-apart constraining elements, including the constraining element of FIG. 13, each of the conductive contacts coupled to a different uncoiled and radially-extended conductor, including the uncoiled and radially-extended conductor of FIG. 13, according to the invention.
Figure 15:
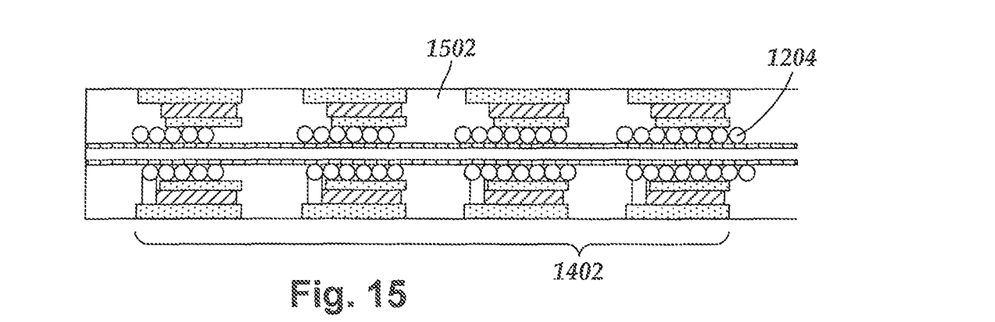
FIG. 15 is a schematic side view of one embodiment of the conductive contact array of FIG. 14 disposed in proximity to the end portion of the conductors of FIG. 13, the conductors encased in a non-conductive material, according to the invention.

FIG. 14 is a schematic longitudinal cross-sectional view of one embodiment of a conductive contact array 1402 disposed over spaced-apart constraining elements 1202 and 1404-1406. In at least some embodiments, the uncoiled portion of at least one of the conductors 1304 and 1408-1410 is electrically coupled directly to one of the conductive contacts of the conductive contact array 1402 (e.g., via welding, soldering, brazing, crimping, swaging, or the like or combinations thereof). In at least some embodiments, the uncoiled portion of at least one of the conductors 1304 and 1408-1410 is electrically coupled (e.g., via welding, soldering, brazing, crimping, swaging, or the like or combinations thereof) to one of the conductive contacts of the conductive contact array 1402 via at least one outer conductive member 1208 and 1412-1414. FIG. 15 is a schematic side view of one embodiment of a non-conductive material 1502 applied over the conductors 1204 and between conductive contacts of the conductive contact array 1402.

Figure 16:
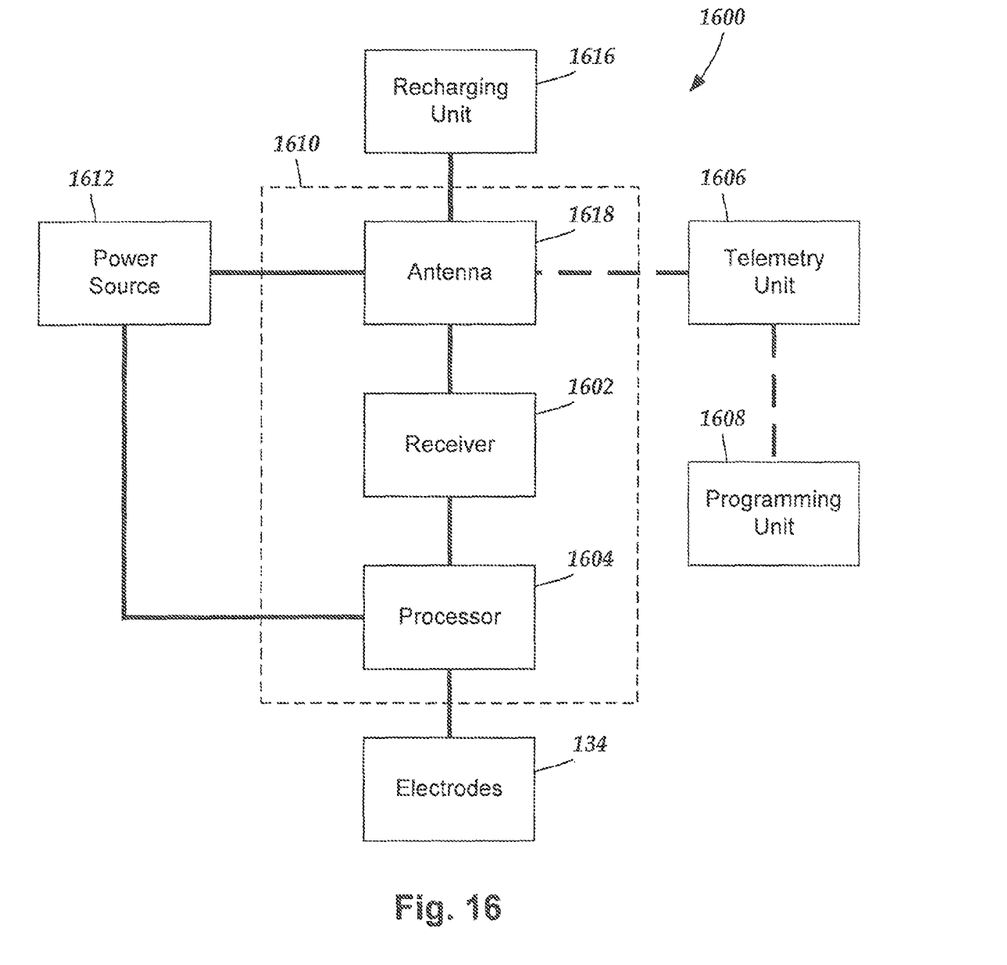
FIG. 16 is a schematic overview of one embodiment of components of a stimulation system, including an electronic subassembly disposed within a control module, according to the invention.

FIG. 16 is a schematic overview of one embodiment of components of an electrical stimulation system 1600 including an electronic subassembly 1610 disposed within a control module. It will be understood that the electrical stimulation system can include more, fewer, or different components and can have a variety of different configurations including those configurations disclosed in the stimulator references cited herein.

Some of the components (for example, power source 1612, antenna 1618, receiver 1602, and processor 1604) of the electrical stimulation system can be positioned on one or more circuit boards or similar carriers within a sealed housing of an implantable pulse generator, if desired. Any power source 1612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1618 or a secondary antenna. The external power source can be in a device that is mounted on the skin of the user or in a unit that is provided near the user on a permanent or periodic basis.

If the power source 1612 is a rechargeable battery, the battery may be recharged using the optional antenna 1618, if desired. Power can be provided to the battery for recharging by inductively coupling the battery through the antenna to a recharging unit 1616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1604 is generally included to control the timing and electrical characteristics of the electrical stimulation system. For example, the processor 1604 can, if desired, control one or more of the timing, frequency, strength, duration, and waveform of the pulses. In addition, the processor 1604 can select which electrodes can be used to provide stimulation, if desired. In some embodiments, the processor 1604 may select which electrode(s) are cathodes and which electrode(s) are anodes. In some embodiments, the processor 1604 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1608 that, for example, allows modification of pulse characteristics. In the illustrated embodiment, the processor 1604 is coupled to a receiver 1602 which, in turn, is coupled to the optional antenna 1618. This allows the processor 1604 to receive instructions from an external source to, for example, direct the pulse characteristics and the selection of electrodes, if desired.

In one embodiment, the antenna 1618 is capable of receiving signals (e.g., RF signals) from an external telemetry unit 1606 which is programmed by a programming unit 1608. The programming unit 1608 can be external to, or part of, the telemetry unit 1606. The telemetry unit 1606 can be a device that is worn on the skin of the user or can be carried by the user and can have a form similar to a pager, cellular phone, or remote control, if desired. As another alternative, the telemetry unit 1606 may not be worn or carried by the user but may only be available at a home station or at a clinician's office. The programming unit 1608 can be any unit that can provide information to the telemetry unit 1606 for transmission to the electrical stimulation system 1600. The programming unit 1608 can be part of the telemetry unit 1606 or can provide signals or information to the telemetry unit 1606 via a wireless or wired connection. One example of a suitable programming unit is a computer operated by the user or clinician to send signals to the telemetry unit 1606.

The signals sent to the processor 1604 via the antenna 1618 and receiver 1602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1600 to cease operation, to start operation, to start charging the battery, or to stop charging the battery. In other embodiments, the stimulation system does not include an antenna 1618 or receiver 1602 and the processor 1604 operates as programmed.

Optionally, the electrical stimulation system 1600 may include a transmitter (not shown) coupled to the processor 1604 and the antenna 1618 for transmitting signals back to the telemetry unit 1606 or another unit capable of receiving the signals. For example, the electrical stimulation system 1600 may transmit signals indicating whether the electrical stimulation system 1600 is operating properly or not or indicating when the battery needs to be charged or the level of charge remaining in the battery. The processor 1604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for forming an implantable lead, the method comprising:
   a) placing a plurality' of elongated conductors into a coiled configuration comprising at least one single-layer region and at least one multi-layer region;
   b) disposing a first constraining element over the plurality of elongated conductors in proximity to an end portion of the plurality of elongated conductors;
   c) uncoiling a first conductor of the plurality of elongated conductors to the first constraining element from a location closer to the end portion than the first constraining element;
   d) disposing a second constraining element over a portion of the plurality of elongated conductors with the second constraining element axially spaced apart from the first constraining element and disposed closer to the end portion than the first constraining element, wherein the uncoiled end of the first conductor extends radially from the elongated conductors between the first constraining element and the second constraining element;
   e) uncoiling a second conductor of the plurality of elongated conductors to the second constraining element from a location closer to the end portion than the second constraining element;
   f) disposing a first conductive contact over the first constraining element;
   g) electrically coupling an uncoiled portion of the first conductor to the first conductive contact; and
   h) disposing a retaining element over a portion of the single-layer region to prevent the multi-layer region from unraveling.

2. The method of claim 1, further comprising disposing a jacket over the multi-layer region.

3. The method of claim 2, wherein disposing the jacket over the multi-layer region comprises disposing the jacket over at least a portion of the retaining element.

4. The method of claim 1, wherein disposing the first constraining element over the plurality of elongated conductors comprises disposing the first constraining element over the single-layer region.

5. The method of claim 1, wherein placing the plurality of elongated conductors into the coiled configuration comprises disposing the elongated conductors over a conductor placement sleeve.

6. The method of claim 1, wherein placing the plurality of elongated conductors into the coiled configuration comprises arranging at least one of the plurality of elongated conductors into at least one unit, the at least one unit comprising
- a first conductor segment extending along the elongated conductors from a beginning point to a first position,
- a second conductor segment extending along the elongated conductors from the first position to a second position, and
- a third conductor segment extending along the elongated conductors from the second position to an endpoint,
- wherein the first position is between the second position and the end point, and the second position is between beginning point and the first position.

7. The method of claim 1, wherein electrically coupling the uncoiled portion of the first conductor to the first conductive contact comprises electrically coupling the uncoiled portion of the first conductor directly to the first conductive contact.

8. The method of claim 1, wherein disposing the first constraining element over the plurality of elongated conductors comprises providing the first constraining element comprising an outer conductive member.

9. The method of claim 8, wherein electrically coupling the uncoiled portion of the first conductor to the first conductive contact comprises electrically coupling the uncoiled portion of the first conductor to the first conductive contact via the outer conductive member.

10. The method of claim 8, wherein disposing the first constraining element over the plurality of elongated conductors comprises providing the first constraining element comprising a protective layer.

11. The method of claim 10, wherein disposing the first constraining element over the plurality of elongated conductors comprises providing the first constraining element with the protective layer disposed over the plurality of elongated conductors, and with the protective layer disposed beneath the outer conductive member.

12. The method of claim 1, wherein disposing the first constraining element over the plurality of elongated conductors comprises disposing a C-shaped first constraining element over the plurality of conductors.

13. The method of claim 1, wherein disposing the first constraining element over the plurality of elongated conductors comprises providing the first constraining element defining at least one slit.

14. The method of claim 1, wherein electrically coupling the uncoiled portion of the first conductor to the first conductive contact comprises removing conductor insulation from the uncoiled portion of the first conductor.

15. The method of claim 1, further comprising
- i) disposing a second conductive contact over the second constraining element; and
- j) electrically coupling an uncoiled portion of the second conductor to the second conductive contact.

16. The method of claim 15, further comprising disposing a non-conductive material over the plurality of elongated conductors placed into the coiled configuration and also between the first conductive contact and the second conductive contact.

17. The method of claim 15, further comprising repeating d), e), i) and j) for a plurality of the second constraining element and for a plurality of the second conductive contact.

* * * * *